(12) United States Patent
Kozuki

(10) Patent No.: US 9,078,439 B2
(45) Date of Patent: Jul. 14, 2015

(54) EMULSIFIABLE CONCENTRATES

(75) Inventor: Yumiko Kozuki, Hyogo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 931 days.

(21) Appl. No.: 12/003,010

(22) Filed: Dec. 19, 2007

(65) Prior Publication Data

US 2008/0153884 A1 Jun. 26, 2008

(30) Foreign Application Priority Data

Dec. 20, 2006 (JP) ................................. 2006-342396

(51) Int. Cl.
  *A01N 43/40* (2006.01)
  *A01P 15/00* (2006.01)

(52) U.S. Cl.
  CPC ..................................... *A01N 43/40* (2013.01)

(58) Field of Classification Search
  None
  See application file for complete search history.

(56) References Cited

U.S. PATENT DOCUMENTS

| 4,751,225 A | 6/1988 | Nishida et al. |
| 6,296,864 B1 | 10/2001 | Zen |

FOREIGN PATENT DOCUMENTS

| EP | 0 839 447 | 5/1998 |
| EP | 0 839 448 | 5/1998 |
| EP | 1 483 967 | 12/2004 |
| ES | 2 251 875 | 5/2006 |
| ES | 2 254 015 | 6/2006 |
| ES | 2 254 016 | 6/2006 |
| WO | 2009/134375 | 11/2009 |
| ZA | 2004/8102 | 7/2005 |
| ZA | 2004/8103 | 7/2005 |
| ZA | 2004/8238 | 7/2005 |
| ZA | 2004/8239 | 7/2005 |
| ZA | 2004/8241 | 7/2005 |

OTHER PUBLICATIONS

Israeli Search Report issued Aug. 10, 2010 in the corresponding Israel Application No. 188060 (with English summary prepared by Applicant's Israeli patent attorney).
French Preliminary Search Report issued Jul. 12, 2010 in corresponding French Application No. 0760059 (with English translation).
Search Report and Written Opinion dated May 7, 2008 in Turkish Patent Application No. 200708875 corresponding to the present U.S. application.
Rejection Decision issued Jul. 4, 2013 in corresponding Taiwan Application No. 096147591 (with English Translation).
Brazilian Office Action dated Aug. 6, 2014 in corresponding Brazilian Patent Application No. PI 0704844-0, with English translation.
Australian Office Action (in English language) issued Jun. 21, 2012 in Australian Application 2007242950 which is a foreign counterpart of the present application.
Office Action issued Sep. 28, 2012 in corresponding Taiwanese Application No. 096147591 (with English Translation).
Notice of Reasons for Rejection issued Jan. 17, 2012 in corresponding Japanese Application No. 2006-342396, with English translation.

*Primary Examiner* — Patricia A Duffy
*Assistant Examiner* — Garen Gotfredson
(74) *Attorney, Agent, or Firm* — Wenderoth, Lind & Ponack, L.L.P.

(57) ABSTRACT

An object of the present invention is to provide an emulsifiable concentrate which comprises pyriproxyfen as an active ingredient, wherein the emulsifiable concentrate is excellent in emulsion stability under conditions of low-rate dilution not only in soft water but also in hard water. The present application provides for an emulsifiable concentrate excellent in emulsion stability which comprises pyriproxyfen, alkylarylsulfonic acid salt, polyoxyethylene styrylphenyl ether, polyoxyethylene castor oil, fatty acid C1-C6 alkyl ester, and aromatic hydrocarbon in specified amounts.

7 Claims, No Drawings

EMULSIFIABLE CONCENTRATES

The present invention relates to an emulsifiable concentrate of pesticide.

BACKGROUND OF THE INVENTION

In an emulsifiable concentrate which is used in the form of emulsion obtained by diluting in water, an emulsifiable concentrate containing fatty acid C1-C6 alkyl ester and aromatic hydrocarbon as solvents is known to be an excellent emulsifiable concentrate which has a low eye-stimulating activity and a high safety (U.S. Pat. No. 6,296,864).

SUMMARY OF THE INVENTION

An object of the present invention is to provide an emulsifiable concentrate which comprises pyriproxyfen as an active ingredient, wherein the emulsifiable concentrate is excellent in the emulsion stability under conditions of low-rate dilution not only in soft water but also in hard water.

The present inventor's various studies for providing an emulsifiable concentrate which comprises pyriproxyfen as an active ingredient, wherein the emulsifiable concentrate is excellent in the emulsion stability under conditions of low-rate dilution not only in soft water but also in hard water, resulted in completion of the present invention.

The present invention is as follows:

[Invention 1]

An emulsifiable concentrate comprising 8 to 30% by weight pyriproxyfen, 1 to 10% by weight alkylarylsulfonic acid salt, 1 to 10% by weight polyoxyethylene styrylphenyl ether, 0.5 to 5% by weight polyoxyethylene castor oil, 10 to 40% by weight fatty acid C1-C6 alkyl ester, and 5 to 79.5% by weight aromatic hydrocarbon, provided that the emulsifiable concentrate is defined to be 100% by weight.

Preferably, it includes, for example, an emulsifiable concentrate substantially consisting of 8 to 30% by weight pyriproxyfen, 1 to 10% by weight alkylarylsulfonic acid salt, 1 to 10% by weight polyoxyethylene styrylphenyl ether, 0.5 to 5% by weight polyoxyethylene castor oil, 10 to 40% by weight fatty acid C1-C6 alkyl ester, and 5 to 79.5% by weight aromatic hydrocarbon, provided that the emulsifiable concentrate is defined to be 100% by weight.

[Invention 2]

An emulsifiable concentrate comprising 8 to 20% by weight pyriproxyfen, 1 to 8% by weight alkylarlylsulfonic acid salt, 1 to 8% by weight polyoxyethylene styrylphenyl ether, 0.5 to 5% by weight polyoxyethylene castor oil, 15 to 40% by weight fatty acid C1-C6 alkyl ester, and 19 to 74.5% by weight aromatic hydrocarbon, provided that the emulsifiable concentrate is defined to be 100% by weight.

Preferably, it includes, for example, an emulsifiable concentrate substantially consisting of 8 to 20% by weight pyriproxyfen, 1 to 8% by weight alkylarylsulfonic acid salt, 1 to 8% by weight polyoxyethylene styrylphenyl ether, 0.5 to 5% by weight polyoxyethylene castor oil, 15 to 40% by weight fatty acid C1-C6 alkyl ester, and 19 to 74.5% by weight aromatic hydrocarbon, provided that the emulsifiable concentrate is defined to be 100% by weight.

[Invention 3]

The emulsifiable concentrate according to Invention 1 or 2, wherein the fatty acid C1-C6 alkyl ester is methyl oleate.

[Invention 4]

The emulsifiable concentrate according to any one of Inventions 1 to 3, wherein the alkylarylsulfonic acid salt is dodecylbenzenesulfonic acid salt.

[Invention 5]

The emulsifiable concentrate according to any one of Inventions 1 to 4, wherein the polyoxyethylene styrylphenyl ether is polyoxyethylene styrylphenyl ether having an HLB of 10 to 15.

[Invention 6]

The emulsifiable concentrate according to any one of Inventions 1 to 5, wherein the polyoxyethylene castor oil is polyoxyethylene castor oil having an HLB of 10 to 15.

The emulsifiable concentrate of the present invention is an emulsifiable concentrate which comprises pyriproxyfen as an active ingredient, wherein the emulsifiable concentrate is excellent in emulsion stability under conditions of low-rate dilution not only in soft water but also in hard water.

DETAILED DESCRIPTION OF THE PREFERRED EMBODIMENTS

The emulsifiable concentrate of the present invention comprises 8 to 30% by weight pyriproxyfen, 1 to 10% by weight alkylarylsulfonic acid salt, 1 to 10% by weight polyoxyethylene styrylphenyl ether, 0.5 to 5% by weight polyoxyethylene castor oil, 10 to 40% by weight fatty acid C1-C6 alkyl ester, and 5 to 79.5% by weight aromatic hydrocarbon, provided that the emulsifiable concentrate is defined to be 100% by weight.

Preferably, the emulsifiable concentrate comprises 8 to 20% by weight pyriproxyfen, 1 to 8% by weight alkylarylsulfonic acid salt, 1 to 8% by weight polyoxyethylene styrylphenyl ether, 0.5 to 5% by weight polyoxyethylene castor oil, 15 to 40% by weight fatty acid C1-C6 alkyl ester and 19 to 74.5% by weight aromatic hydrocarbon, provided that the emulsifiable concentrate is defined to be 100% by weight.

Pyriproxyfen is a pesticidal compound disclosed in U.S. Pat. No. 4,751,225, and produced according to the description or available in the market.

The alkylarylsulfonic acid salt is an anionic surfactant having at least one sulfonic acid salt in the molecule. The alkyl group of the alkylarylsulfonic acid salt used in the present invention is usually an alkyl group having 8 to 15 carbon atoms. The salt of the alkylarylsulfonic acid salt includes, for example, alkali metal salts such as a sodium salt and a potassium salt, alkaline earth metal salts such as a calcium salt and a magnesium salt, and an amine salt.

The alkylarylsulfonic acid salt used in the present invention includes, for example, alkylbenzenesulfonic acid salt, and specifically sodium dodecylbenzenesulfonate and calcium dodecylbenzenesulfonate.

The emulsifiable concentrate of the present invention comprises 1 to 10% by weight, preferably 1 to 8% by weight the alkylarylsulfonic acid salt.

The polyoxyethylene styrylphenyl ether is a nonionic surfactant, and the polyoxyethylene styrylphenyl ether used in present invention includes, for example, polyoxyethylene distyrylphenyl ether and polyoxyethylene tristyrylphenyl ether. Polyoxyethylene tristyrylphenyl ether is preferably used in terms of the availability.

An HLB of the polyoxyethylene styrylphenyl ether used in the present invention is preferably 10 to 15, and more preferably 11 to 14. The HLB means a hydrophilic-lipophilic balance and it is well-known in the art of surfactant.

The emulsifiable concentrate of the present invention comprises 1 to 10% by weight, preferably 1 to 8% by weight the polyoxyethylene styrylphenyl ether.

The polyoxyethylene castor oil is a nonionic surfactant, and it is a chemical compound obtained by additive polymerization between ethylene oxide and castor oil in the presence of a base.

An HLB of the polyoxyethylene castor oil used in the present invention is preferably 10 to 15, and more preferably 11 to 14.

The emulsifiable concentrate of the present invention comprises 0.5 to 5% by weight the polyoxyethylene castor oil.

The fatty acid C1-C6 alkyl ester used in the present invention includes methyl ester, ethyl ester, propyl ester, isopropyl ester, butyl ester, isobutyl ester and isopentyl ester of carboxylic acid such as propionic acid, butyric acid, isobutyric acid, isovaleric acid, lauric acid, myristic acid, palmitic acid, capric acid, oleic acid, linoleic acid or linolenic acid, and preferably, includes, for example, methyl oleate, methyl palmitate, methyl laurate, isopropyl myristate, isopropyl palmitate and butyl stearate.

The emulsifiable concentrate of the present invention comprises 10 to 40% by weight, preferably 15 to 40% by weight the fatty acid C1-C6 alkyl ester.

The aromatic hydrocarbon used in the present invention includes, for example, alkylbenzene such as toluene, dialkylbenzene such as xylene, alkylnaphthalene such as methylnaphthalene, dialkylnaphthalene such as dimethylnaphthalene, trialkylnaphthalene such as dimethylmonoisopropylnaphthalene, and phenylxylylethane.

In the present invention, as the aromatic hydrocarbon, a commercially available solvent can be used as it is, and such commercially available solvent includes, for example, Nisseki Hisol SAS-296 (a mixture of 1-phenyl-1-xylylethane and 1-phenyl-1-ethylphenylethane, the trade name of Nippon Oil Corporation), Cactus Solvent HP-MN (methylnaphthalene 80%, the trade name of Japan Energy Corporation), Cactus Solvent HP-DMN (dimethylnaphthalene 80%, the trade name of Japan Energy Corporation), Cactus Solvent P-100 (alkylbenzene having 9 to 10 carbon atoms, the trade name of Japan Energy Corporation), Cactus Solvent P-150 (alkylbenzene, the trade name of Japan Energy Corporation), Cactus Solvent P-180 (a mixture of methylnaphthalene and dimethylnaphthalene, the trade name of Japan Energy Corporation), Cactus Solvent P-200 (a mixture of methylnaphthalene and dimethylnaphthalene, the trade name of Japan Energy Corporation), Cactus Solvent P-220 (a mixture of methylnaphthalene and dimethylnaphthalene, the trade name of Japan Energy Corporation), Cactus Solvent PAD-1 (dimethylmonoisopropylnaphthalene, the trade name of Japan Energy Corporation), Solvesso 100 (aromatic hydrocarbon, the trade name of Exxon Mobil Corporation), Solvesso 150 (aromatic hydrocarbon, the trade name of Exxon Mobil Corporation), Solvesso 200 (aromatic hydrocarbon, the trade name of Exxon Mobil Corporation), ULTRA LOW NAPHTHALENE AROMATIC 150 (ExxonMobil Chemical Company), ULTRA LOW NAPHTHALENE AROMATIC 200 (ExxonMobil Chemical Company), Solvesso 150 ND (aromatic hydrocarbon, the trade name of Exxon Mobil Corporation), Solvesso 200 ND (aromatic hydrocarbon, the trade name of Exxon Mobil Corporation), Swasol 100 (toluene, the trade name of Maruzen Petrochemical Co. Ltd.), and Swasol 200 (xylene, the trade name of Maruzen Petrochemical Co. Ltd.).

The emulsifiable concentrate of the present invention usually comprises 5 to 79.5% by weight, preferably 19 to 74.5% by weight the aromatic hydrocarbon.

The preferable weight proportion of components includes, for example, pyriproxyfen:alkylarylsulfonic acid salt:polyoxyethylene styrylphenyl ether:polyoxyethylene castor oil: fatty acid C1-C6 alkyl ester:aromatic hydrocarbon=8 to 20% by weight: 1 to 8% by weight: 1 to 8% by weight: 0.5 to 5% by weight: 15 to 40% by weight: 19 to 74.5% by weight.

The emulsifiable concentrate of the present invention may further comprise optionally other solvents, adjuvants, an antioxidant, a flavoring agent, a colorant and the like.

The emulsifiable concentrate of the present invention can be produced, for example, by stirring pyriproxyfen, alkylarylsulfonic acid salt, polyoxyethylene styrylphenyl ether, polyoxyethylene castor oil, fatty acid C1-C6 alkyl ester and aromatic hydrocarbon until they become uniform, as necessary, with heating (at 80° C. or lower). Additionally, other solvents, adjuvants or the like may be optionally mixed therein.

The emulsifiable concentrate of the present invention is usually diluted with water, and is applied to pests or places where pests habit. That is, for example, the emulsifiable concentrate of the present invention is applied by diluting with water from 10- to 5000-fold and spraying the dilution to plants and/or a soil where pests inhabit. Alternatively, the emulsifiable concentrate of the present invention diluted with water from 10- to 1000-fold may be aerially-sprayed via a helicopter.

An amount of the emulsifiable concentrate of the present invention to be applied is usually 0.1 to 1000 g/10 a, preferably 1 to 100 g/10 a as expressed by an amount of pyriproxyfen.

BRIEF DESCRIPTION OF THE DRAWINGS

The patent or application file contains at least one drawing executed in color. Copies of this patent or patent application publication with colored drawing(s) will be provided by the Office upon request and payment of the necessary fee.

EXAMPLES

The following Preparation Examples and Test Example more specifically illustrate the present invention, but these examples are not intended to limit the scope of the present invention.

Preparation Example 1

At 20° C., 10.3 g of pyriproxyfen, 4.0 g of calcium dodecylbenzenesulfonate (Rhodacal 60/BE, manufactured by Rhodia Nicca Ltd.), 4.0 g of polyoxyethylene tristyrylphenyl ether (Soprophor BSU, HLB: 12.5, manufactured by Rhodia Nicca Ltd.), 1.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 1 of the present invention.

Preparation Example 2

At 20° C., 10.3 g of pyriproxyfen, 4.0 g of calcium dodecylbenzenesulfonate (Rhodacal 60/BE, manufactured by Rhodia Nicca Ltd.), 3.0 g of polyoxyethylene tristyrylphenyl ether (Soprophor BSU, HLB: 12.5, manufactured by Rhodia Nicca Ltd.), 2.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 2 of the present invention.

Preparation Example 3

At 20° C., 10.3 g of pyriproxyfen, 4.0 g of calcium dodecylbenzenesulfonate (Rhodacal 60/BE, manufactured by Rhodia Nicca Ltd.), 2.0 g of polyoxyethylene tristyrylphenyl ether (Soprophor BSU, HLB: 12.5, manufactured by Rhodia Nicca Ltd.), 3.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 3 of the present invention.

Preparation Example 4

At 20° C., 10.3 g of pyriproxyfen, 4.0 g of calcium dodecylbenzenesulfonate (Rhodacal 60/BE, manufactured by Rhodia Nicca Ltd.), 1.0 g of polyoxyethylene tristyrylphenyl ether (Soprophor BSU, HLB: 12.5, manufactured by Rhodia Nicca Ltd.), 4.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 4 of the present invention.

Preparation Example 5

At 20° C., 10.3 g of pyriproxyfen, 4.0 g of calcium dodecylbenzenesulfonate (Rhodacal 60/BE, manufactured by Rhodia Nicca Ltd.), 2.0 g of polyoxyethylene tristyrylphenyl ether (Soprophor BSU, HLB: 12.5, manufactured by Rhodia Nicca Ltd.), 2.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 5 of the present invention.

Preparation Example 6

At 20° C., 10.3 g of pyriproxyfen, 4.0 g of calcium dodecylbenzenesulfonate (Rhodacal 60/BE, manufactured by Rhodia Nicca Ltd.), 3.4 g of polyoxyethylene tristyrylphenyl ether (Soprophor BSU, HLB: 12.5, manufactured by Rhodia Nicca Ltd.), 1.6 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 6 of the present invention.

Preparation Example 7

At 20° C., 10.3 g of pyriproxyfen, 3.11 g of calcium dodecylbenzenesulfonate (Rhodacal 60/BE, manufactured by Rhodia Nicca Ltd.), 3.11 g of polyoxyethylene tristyrylphenyl ether (Soprophor BSU, HLB: 12.5, manufactured by Rhodia Nicca Ltd.), 0.78 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 7 of the present invention.

Preparation Example 8

At 20° C., 10.3 g of pyriproxyfen, 4.0 g of calcium dodecylbenzenesulfonate (Rhodacal 60/BE, manufactured by Rhodia Nicca Ltd.), 1.0 g of polyoxyethylene tristyrylphenyl ether (Soprophor BSU, HLB: 12.5, manufactured by Rhodia Nicca Ltd.), 3.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 8 of the present invention.

Preparation Example 9

At 20° C., 10.3 g of pyriproxyfen, 4.0 g of calcium dodecylbenzenesulfonate (Rhodacal 60/13E, manufactured by Rhodia Nicca Ltd.), 1.0 g of polyoxyethylene tristyrylphenyl ether (Soprophor BSU, HLB: 12.5, manufactured by Rhodia Nicca Ltd.), 3.5 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 9 of the present invention.

Preparation Example 10

At 20° C., 10.3 g of pyriproxyfen, 4.0 g of calcium dodecylbenzenesulfonate (Witconate P-1860, manufactured by Akzo Nobel), 4.0 g of polyoxyethylene tristyrylphenyl ether (Soprophor BSU, HLB: 12.5, manufactured by Rhodia Nicca Ltd.), 1.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 10 of the present invention.

Preparation Example 11

At 20° C., 10.3 g of pyriproxyfen, 4.0 g of calcium dodecylbenzenesulfonate (Rhodacal 60/BE, manufactured by Rhodia Nicca Ltd.), 3.0 g of polyoxyethylene tristyrylphenyl ether (Soprophor BSU, HLB: 12.5, manufactured by Rhodia Nicca Ltd.), 1.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150ND, manufactured by Exxon Mobil Corporation) was added so that the total weight is 100 g, and stirred until it becomes a homogeneous solution to give the emulsifiable concentrate 11 of the present invention.

Preparation Example 12

At 20° C., 15.0 g of pyriproxyfen, 4.0 g of calcium dodecylbenzenesulfonate (Rhodacal 60/BE, manufactured by Rhodia Nicca Ltd.), 4.0 g of polyoxyethylene tristyrylphenyl ether (Soprophor BSU, HLB: 12.5, manufactured by Rhodia Nicca Ltd.), 1.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 12 of the present invention.

Preparation Example 13

At 20° C., 30.0 g of pyriproxyfen, 4.0 g of calcium dodecylbenzenesulfonate (Rhodacal 60/BE, manufactured by Rhodia Nicca Ltd.), 4.0 g of polyoxyethylene tristyrylphenyl ether (Soprophor BSU, HLB: 12.5, manufactured by Rhodia Nicca Ltd.), 1.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 13 of the present invention.

Preparation Example 14

At 20° C., 15.0 g of pyriproxyfen, 4.0 g of calcium dodecylbenzenesulfonate (Rhodacal 60/BE, manufactured by Rhodia Nicca Ltd.), 1.0 g of polyoxyethylene tristyrylphenyl ether (Soprophor BSU, HLB: 12.5, manufactured by Rhodia Nicca Ltd.), 3.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 14 of the present invention.

Preparation Example 15

At 20° C., 30.0 g of pyriproxyfen, 4.0 g of calcium dodecylbenzenesulfonate (Rhodacal 60/BE, manufactured by Rhodia Nicca Ltd.), 1.0 g of polyoxyethylene tristyrylphenyl ether (Soprophor BSU, HLB: 12.5, manufactured by Rhodia Nicca Ltd.), 3.0 g of polyoxyethylene castor oil (Berol 904, HLB: 13, manufactured by Akzo Nobel), and 30.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 15 of the present invention.

Preparation Example 16

At 20° C., 10.3 g of pyriproxyfen, 4.0 g of calcium dodecylbenzenesulfonate (Rhodacal 60/BE, manufactured by Rhodia Nicca Ltd.), 4.0 g of polyoxyethylene tristyrylphenyl ether (Soprophor BSU, HLB: 12.5, manufactured by Rhodia Nicca Ltd.), 1.0 g of polyoxyethylene castor oil (Berol 904, HLB: 13, manufactured by Akzo Nobel), and 40.0 g of methyl oleate (EXCEPARL M-OL, manufactured by Kao Corporation) were placed in a 100-ml measuring flask, and then, aromatic hydrocarbon (Solvesso 150, manufactured by Exxon Mobil Corporation) was added so that the total weight is 100 g, and stirred until it becomes a homogeneous solution to give the emulsifiable concentrate 16 of the present invention.

Test Example regarding emulsification stability of the emulsifiable concentrate of the present invention will be shown below.

Test Example 3.04 g Of calcium chloride and 1.39 g of magnesium chloride hexahydrate were dissolved in water to prepare 100 ml of a hard water stock solution for test.

0.59 ml Of the hard water stock solution was diluted to prepare 1000 ml of soft water for test having the hardness of 20 ppm. Similarly, 100 ml of the hard water stock solution was diluted to prepare 1000 ml of hard water for test having the hardness of 342 ppm.

95 ml Of the soft water for test having the hardness of 20 ppm was placed in a 100-ml stoppered measuring cylinder, and left in a thermoregulated water bath at 30° C. for a while to adjust the water temperature to 30° C. Then, 5 ml of the emulsifiable concentrate of the present invention obtained in each of the above Preparation Examples was added into the measuring cylinder, and the measuring cylinder was inverted ten times at a rate of once for 2 seconds, and then left again in a thermoregulated water bath at 30° C. for 2 hours.

After that, when the state of an emulsion in the measuring cylinder was observed, it was found that, regarding all of the emulsifiable concentrates 1 to 16 of the present invention, a homogeneously emulsified state was retained, or only a trace amount of cream-like separation was observed.

In addition, similarly, when the state of the emulsion obtained by using the hard water for test having the hardness of 342 ppm was observed, it was found that, regarding all of the emulsifiable concentrates 1 to 16 of the present invention, a homogeneously emulsified state was retained, or only a trace amount of cream-like separation was observed.

The emulsifiable concentrates of the present invention are an emulsifiable concentrate which comprises pyriproxyfen as an active ingredient, and is excellent in emulsion stability under conditions of low-rate dilution not only in soft water but also in hard water.

What is claimed is:
1. An emulsifiable concentrate comprising 8 to 30% by weight pyriproxyfen, 1 to 10% by weight calcium dodecylbenzenesulfonate, 1 to 10% by weight polyoxyethylene styrylphenyl ether, 0.5 to 5% by weight polyoxyethylene castor oil, 10 to 40% by weight methyl oleate, and 5 to 79.5% by weight heavy aromatic naphtha, provided that the emulsifiable concentrate is defined to be 100% by weight.

2. An emulsifiable concentrate comprising 8 to 20% by weight pyriproxyfen, 1 to 8% by weight calcium dodecylbenzenesulfonate, 1 to 8% by weight polyoxyethylene styrylphenyl ether, 0.5 to 5% by weight polyoxyethylene castor oil, 15 to 40% by weight methyl oleate, and 19 to 74.5% by weight heavy aromatic naphtha, provided that the emulsifiable concentrate is defined to be 100% by weight.

3. The emulsifiable concentrate according to claim 1, wherein the polyoxyethylene styrylphenyl ether is polyoxyethylene styrylphenyl ether having an HLB of 10 to 15.

4. The emulsifiable concentrate according to claim 1, wherein the polyoxyethylene castor oil is polyoxyethylene castor oil having an HLB of 10 to 15.

5. The emulsifiable concentrate according to claim 2, wherein the polyoxyethylene styrylphenyl ether is polyoxyethylene styrylphenyl ether having an HLB of 10 to 15.

6. The emulsifiable concentrate according to claim 2, wherein the polyoxyethylene castor oil is polyoxyethylene castor oil having an HLB of 10 to 15.

7. The emulsifiable concentrate according to claim 3, wherein the polyoxyethylene castor oil is polyoxyethylene castor oil having an HLB of 10 to 15.

\* \* \* \* \*